United States Patent [19]

Abu Seir et al.

[11] Patent Number: 5,827,544
[45] Date of Patent: Oct. 27, 1998

[54] DIFFERENT WAY OF MANAGEMENT OF NEONATAL HYPERBILIRUBINEMIA

[75] Inventors: Husni H. Abu Seir; Wael F. Sunnoqrot; Bassam M. El-Wadi, all of Amman, Jordan

[73] Assignee: The Arab Pharmaceutical Manufacturing Co. Ltd., Sult-Jordan

[21] Appl. No.: 720,773

[22] Filed: Oct. 3, 1996

Related U.S. Application Data

[60] Provisional application No. 60/004,991 Oct. 10, 1995.
[51] Int. Cl.$^6$ .................................................... A01N 59/08
[52] U.S. Cl. ........................ 424/677; 424/439; 424/94.4; 514/440; 426/34
[58] Field of Search .................................. 424/439, 94.4, 424/677; 514/440; 426/34

[56] References Cited

U.S. PATENT DOCUMENTS

| | | | |
|---|---|---|---|
| 4,968,495 | 11/1990 | Inoue | 424/94.4 |
| 5,254,572 | 10/1993 | Serfontein | 514/345 |
| 5,569,670 | 10/1996 | Weischer | 514/440 |
| 5,569,675 | 10/1996 | Rephaeli | 514/547 |

*Primary Examiner*—Carlos A. Azpuru
*Assistant Examiner*—D. Faulkner
*Attorney, Agent, or Firm*—Ladas & Parry

[57] ABSTRACT

A method for treatment and prevention of neonatal hyperbilirubinemia by oral administration of a preparation to treat and prevent neonatal hyperbilirubinemia. A preparation that can be used includes castor oil, honey and cellulose fibers. Another preparation that can be used includes castor oil, cellulose fibers, magnesium and vitamin $B_2$. The magnesium may be in the form of magnesium salts, magnesium oxides or any other form suitable for use in newborns.

23 Claims, No Drawings

DIFFERENT WAY OF MANAGEMENT OF NEONATAL HYPERBILIRUBINEMIA

This application claims the benefit of U.S. Provisional Application No.: 60/004,991 filing date Oct. 10, 1995.

FIELD OF THE INVENTION

It is very important to find a safe and effective way to manage neonatal hyperbilirubinemia (referred to hereinafter as NHB) since nearly 50% of all newborns in the world develop clinical jaundice and more than 6% of newborns require hospitalization because of this condition.

The present invention relates to a method for treatment and prevention of neonatal hyperbilirubinemia by administering a composition that can treat and prevent neonatal hyperbilirubinemia. A composition that can be used comprises castor oil, honey and cellulose fibers. Another composition that can be used comprises castor oil, cellulose fibers, magnesium and vitamin $B_2$. Other types of compositions that can be used are also described.

DESCRIPTION OF PRIOR ART

Prior art teaches the following methods to treat neonatal hyperbilirubinemia:

A) PHOTOTHERAPY

It is generally considered when total serum bilirubin (T.S.B.) is >15 mg/dL in full term newborns and >12 mg/dL in pre term newborns.

If there are other criteria such as possible Rh and ABO incompatibility or early rapid increase in T.S.B., phototherapy is administered when T.S.B. is at a much lower level.

It converts the indirect bilirubin to photobilirubin which is easily excreted by the liver. It acts on the outer 2 mm. of skin.

Photobilirubin is unstable and may revert to indirect bilirubin in the darkness of the gallbladder and intestines and thus about 65% of excreted bilirubin may be reabsorbed especially from the duodenum.

Phototherapy is used mainly in hospitals for inpatient newborns. It is costly, it has psychological effects on both the baby and the mother because of the separation of the mother and baby from each other. Other complications of phototherapy are hyperpyrexia, water loss, and rash. The use of a fiberoptic blanket at home, makes the parents anxious because the baby is put in an electrical apparatus. The length of the fiber optic blanket cord is an additional problem.

B) EXCHANGE TRANSFUSION

In severe cases of NHB double volume blood exchange transfusion is performed (2×85 ml/kg) to lower the high level of T.S.B. rapidly.

Exchange transfusion is indicated:
When cord bilirubin is >5 mg/dL.
When postnatal increase in T.S.B. is >1 mg/dL/hour.
When T.S.B. is >20 mg/dL in average newborn.

If there are other criteria such as prematurity, hypoxia and acidosis, exchange transfusion is done when T.S.B. level is at a much lower level. After exchange transfusion T.S.B. drops to 50% of the preexchange level, but a few hours later it may rebound to 30–50% due to equilibrium of the serum with extravascular bilirubin in tissues.

C) METALLOPORPHYRINS (Zn, Sn, Mn, Ni, and Cr)

Administration of metalloporphyrin to the newborns with neonatal hyperbilirubinemia (NHB) inhibits the enzyme cytosomal heme oxygenase which transfers protoporphyrin (heme) to bilirubin. The affinity of metalloporphyrins to the enzyme is 500 times more than that of heme to the enzyme.

Heme is found in every cell in the body and is present in myoglobins, cytochromes and cellular catalase.

Metalloporphyrins are photosensitizers and their effect on the cytosomal heme oxygenase is long lasting (greater than 12 days). They displace intracellular hemes, causing partial loss of cellular enzymatic activity for a relatively long time, which may have undesirable effects on a developing newborn.

D) INDUCTIVE DRUGS AS PHENOBARBITONE, FLUMECINOLONE and ZIXORYN

They activate glucuronyl transferase enzyme. The effect of phenobarbitone on lowering T.S.B. does not appear until several days after administration, and because of its sedative effect, it may cause lethargy in the newborn.

E) CHITOSAN SALTS

These act as cellulose and can adsorb bilirubin. They are not given with milk because they precipitate milk proteins.

DESCRIPTION OF THE INVENTION

Applicants' antihyperbilirubinemia preparations are natural and safe. Collectively, these preparations will be referred to as AHB preparations. One preparation is composed of three active ingredients and other additives. The three active ingredients are: castor oil, honey and cellulose fibers. Optionally, the specifications of the three active ingredients are according to the British Pharmacopoeia. This preparation will be referred to as the AHB-1 preparation. Another AHB preparation comprises the active ingredients of castor oil, cellulose fibers, magnesium and vitamin $B_2$. The magnesium may be in the form of magnesium salts, magnesium oxides or any other form suitable for use in newborns.

All of these preparations can be prepared in various forms including gels and suspensions.

DOSAGE

All of the preparations are easy to administer and can be given to inpatients and outpatients by mixing with milk (breast or humanized). Humanized milk is milk that simulates human breast milk like infant formulas. Examples of humanized milk are packaged infant formulas.

The daily dosage of the preparations is 5 ml of gel or suspension per kg of body weight in three equal doses. The daily dosage of the AHB-1 preparation is 5 ml of gel or suspension per kg of body weight in three equal doses.

The dose is preferably given with 10–15 ml breast or humanized milk to insure cholagogue action. This gives the maximal effect of the preparation in treating intestinal bilirubins. The preparations can also be given with pre-mixed infant formula.

SUGGESTED MECHANISM OF ACTION

Castor oil, Honey and Cellulose fibers act together and have systemic and local actions. Many clinical tests were conducted, and tests were conducted where one or two of the active ingredients were excluded. Following the completion of these clinical tests applicants concluded that the three said ingredients are active and cause rapid drop in T.S.B. Other tests indicated that a preparation containing castor oil, cellulose fibers, magnesium and vitamin $B_2$ also caused a drop in T.S.B.

It is preferred that the pH of the preparations be from about 4.5 to 5.5.

AHB preparations, furthermore, eliminate bilirubins by affecting the whole pathway of bilirubin metabolism. The systemic and local actions of AHB preparations are:

1—The preparations provide immediate energy for the newborn. This energy is vital to the brain, metabolism of red blood cells, conjugation and excretion of bilirubin.

2—The AHB-1 preparation has vitamins ($B_2$ & E) and minerals (Na, Ca, K and Mg). These are important for balanced osmosis inside and outside the red blood cells and for maintaining the integrity of the cellular membrane of the red blood cells. The other AHB preparation has vitamins ($B_2$ & E) and Mg. Na and K are found in breast milk, humanized milk and pre-mixed infant formula.

3—Hepatic Phase: The preparations give energy for hepatic uptake, conjugation and excretion of bilirubin.

4—Intestinal Phase: The preparations help in absorption and/or adsorption and expulsion of bilirubins.

CASTOR OIL

Fat splitting enzymes are relatively deficient in the newborn. Pancreatic lipase is not produced by the newborn (first month of life), only Lingual lipase is present. Thus Castor oil is partially hydrolyzed in the intestines, and the result is ricin oleic acid (ROA) and glycerin. The former causes mild irritation of the mucous membrane of the intestines and increases peristalsis, but it does not cause diarrhea. The castor oil leads to excretion of all intestinal bilirubins, "direct, indirect, and photo" due to its effect of increasing peristalsis. Ricin oleic acid (ROA) is absorbed and metabolized as any fatty acid leading to an increase in energy.

Castor oil contains about 3–12 mg vitamin E/100 gm of castor oil. Part of vitamin E is absorbed. Vitamin E deficiency increases the sensitivity of red blood cells to hemolysis in the presence of hydrogen peroxide. Vitamin E improves hemolysis of red blood cells in G6PDD (Glucose—6—Phosphate—Dehydrogenase Deficiency).

HONEY (clostridium botulinum spores free)

The caloric need of the average newborn is 300 calories/day. It comes from:

Carbohydrates

Fats

Proteins

Glycogen stored in the liver of the newborn yields only 100 calories, which accounts for about 8 hours energy consumption of the newborn. The brain depends totally on liver glycogen and glucose for its energy. The liver, muscles and heart may utilize free fatty acids. Intestinal amylase may be decreased during the first four months of life, and this causes limited decrease in hydrolysis of the polysaccharides.

Honey has local and systemic actions.

A) Local action

Mild laxative effect of polysaccharides which helps in expulsion of intestinal bilirubins.

B) Systemic action

Additional energy of polysaccharides in Honey.

Electrolytes in Honey as (Mg, Na and K) which are important for maintaining the integrity of red blood cell membrane.

Vitamin $B_2$ "riboflavin" found in Honey is important in changing indirect bilirubin to photo bilirubin.

In those preparations where honey is not used, magnesium and vitamin $B_2$ are added. Magnesium may also be added to the AHB-1 preparation. Magnesium may be in the form of salts, oxides or any other form that is suitable for use in newborns.

CELLULOSE FIBERS

Two kinds of Cellulose fibers may be used in AHB preparations. These are: dispersible cellulose and microcrystalline cellulose, and they are used in the preparation for the following local actions:

To remove intestinal bilirubins by absorption and/or adsorption.

To increase roughage and peristalsis and consequently accelerate the expulsion of intestinal bilirubins.

Note—In addition to the above purposes, dispersible cellulose is also used as a gelling agent.

The present invention is described with respect to the following examples. These are provided for illustrative purposes only and are not to be construed as limitations of the invention.

EXAMPLE 1

COMPOSITION

The three active ingredients of AHB-1 preparation (in gel form) with their percentages are as follows: (percentages are weight percent)

| | |
|---|---|
| Castor oil | 10–50% preferably 40% |
| Honey | 5–40% preferably 10% |
| Cellulose fibers: | |
| Dispersible cellulose | 1–3% preferably 2% |
| Microcrystalline cellulose | 2–6% preferably 4% |

EXAMPLE 1A

An AHB-1 preparation (in gel form) (expressed in gm per 100 gm of the preparation) is as follows:

| | |
|---|---|
| Castor oil (active ingredient) | 40 |
| Butylated hydroxy anisole (antioxidant) | 0.015 |
| Dispersible cellulose (active ingredient and gelling agent) | 2 |
| Xanthan gum (stabilizer) | 0.3 |
| Microcrystalline cellulose (active ingredient) | 4 |
| Honey (active ingredient) | 10 |
| Potassium sorbate (preservative) | 0.2 |
| Citric acid (to adjust pH) | 0.12 |
| Milk flavor (flavoring agent) | 0.1 |
| Distilled water Q.S add | 100 |

Note—to produce suspension form: decrease dis-persible cellulose by 0.5 gm and increase microcrystalline cellulose by the same quantity (i.e. 0.5 gm).

Castor oil (BP)—British Pharmacopoeia volume I, P. 117, 1993.

Honey [Purified honey (BP)]—British Pharmacopoeia volume I, P. 328, 1993.

Dispersible cellulose (BP)—British Pharmacopoeia volume I, P. 119, 1993.

Microcrystalline cellulose (BP)—British Pharmacopoeia volume I, P. 119, 1993.

EXAMPLE 1B

The active ingredients of the other disclosed AHB preparation (in gel form) is

| | |
|---|---|
| Castor Oil<br>Cellulose Fibers: | 10–50% preferably 40% |
| Dispersible cellulose | 1–3% preferably 2% |
| Microcrystalline cellulose | 2–6% preferably 4% |
| Magnesium | 0.0010 to<br>0.0100 gm/100 gm of preparation |
| Vitamin $B_2$ | 0.00010 to<br>0.00100 gm/100 gm of preparation |

(the percentages are weight percent)

In a preferred embodiment the amount of magnesium oxide is 0.00547 gm/100 gm of the preparation; the amount of vitamin $B_2$ is 0.00041 gm/100 gm of the preparation, and the amount of an emulsifying agent is 0.1 g/100 gm of the preparation.

EXAMPLE 1C

An AHB preparation (in gel form) (expressed in gm per 100 gm of the preparation) is as follows:

| | |
|---|---|
| Castor Oil (active ingredient) | 40 |
| Butylated hydroxy anisole (antioxidant) | 0.015 |
| Dispersible cellulose (active ingredient and gelling agent) | 2 |
| Xanthan gum (stabilizer) | 0.3 |
| Microcrystalline cellulose (active ingredient) | 4 |
| Potassium sorbate (preservative) | 0.2 |
| Citric acid (to adjust pH) | 0.12 |
| Milk flavor (flavoring agent) | 0.1 |
| Magnesium oxide | 0.00547 |
| Vitamin $B_2$ | 0.00041 |
| Emulsifying agent | 0.1 |
| Distilled water Q.S add | 100 |

Note—to produce suspension form: decrease dispersible cellulose by 0.5 gm and increase microcrystalline cellulose by the same quantity (i.e. 0.5 gm).

Castor oil (BP)—British Pharmacopoeia volume I, P. 117, 1993.

Dispersible cellulose (BP)—British Pharmacopoeia volume I, P. 119, 1993.

Microcrystalline cellulose (BP)—British Pharmacopoeia volume I, P. 119, 1993.

EXAMPLE 2

METHOD OF PREPARATION OF GEL OR SUSPENSION OF AHB-1

1—Disperse dispersible cellulose and xanthan gum in 40 ml distilled water. Mix for 15 minutes.

2—Add microcrystalline cellulose and mix for 15 minutes.

3—Heat honey up to (50°–60° C.). Add and mix for 10 minutes.

4—Dissolve potassium sorbate in 1.5 ml distilled water. Add and mix for 10 minutes.

5—Dissolve citric acid in 1.765 ml distilled water. Add and mix for 5 minutes.

6—Dissolve milk flavor in 1.5 ml distilled water. Add and mix for 5 minutes.

7—Heat castor oil and butylated hydroxy anisole up to (60°–70° C.). Add and mix for 20 minutes. Check pH and adjust by citric acid to be (4.5–5.5).

Final preparation is checked to be clostridium botulinum spore free by the special test mentioned in (FDA Bacteriological Analytical Manual, 7th Edition, P. 215–225, 1992). Preparation should be clostridium botulinum spore free to prevent infant botulism.

EXAMPLE 2A

METHOD OF PREPARATION OF ANOTHER AHB PREPARATION

1—Disperse dispersible cellulose and xanthan gum in 40 ml distilled water. Mix for 15 minutes.

2—Add microcrystalline cellulose and mix for 15 minutes.

3—Add and disperse magnesium oxide and mix for 10 minutes. Dissolve vitamin $B_2$ in about 5 ml of distilled water. Add and mix for 10 minutes.

4—Dissolve potassium sorbate in 1.5 ml distilled water. Add and mix for 10 minutes.

5—Dissolve citric acid in 1.765 ml distilled water. Add and mix for 5 minutes.

6—Dissolve milk flavor in 1.5 ml distilled water. Add and mix for 5 minutes.

7—Heat castor oil and butylated hydroxy anisole up to (60°–70° C.). Add and mix for 20 minutes. Check pH and adjust by citric acid to be (4.5–5.5). Add 0.1 gm of emulsifying agent.

INTRODUCTION TO EXAMPLES 3 AND 4

DEALING WITH TESTS FOR THE TOXICITY OF AHB PREPARATION

According to Article 2-2 of the 1986 WHO act (Guidelines for the Assessment of Herbal medicine, 7th Draft, Feb. 8th, 1991), concerning safety and quality of herbal remedies, if long term traditional use of the compound or compositions cannot be documented, toxicity data have to be submitted. The active constituents of AHB preparations are of well known natural and plant origins, and have been used for hundreds of years in folk medicine and in food stuffs, and many studies have been done on these constituents. Nevertheless, the following toxicity study of Examples 3 & 4 was conducted to complete the overall study.

MATERIALS AND METHODS

PREPARATION PHASE

This study was carried out on a total of 20 healthy rabbits each weighing 0.9–1.0 Kg. and 60 healthy mice each weighing 18–20 gm. The rabbits were placed in separate cages while the mice were placed in 6 cages (10 in each).

These animals were observed for a period of two weeks to ensure their acclimatization to the laboratory environment.

EXAMPLE 3

LD50 STUDY (TEST ON MICE)

This study was carried out for a period of 48 hours. Mice were randomly divided into two groups of 30 mice each (treatment and control group). This study assessed the LD50 of AHB-1 preparation comprising castor oil, honey and cellulose fibers. Dose: A single dose of 15 gm (=15 ml) of AHB-1 preparation per Kg of the animal weight, in suspension form, was given orally for each animal.

EXAMPLE 4

ACUTE STUDY (TEST ON RABBITS)

This study was carried out for a period of 7 days. Rabbits were randomly divided into two groups of 10 animals each (treatment and control group). This study assessed the oral toxicity effect of AHB-1 preparation. Dosage: A dosage of 5 ml of AHB-1 preparation/kg of animal body weight/day, in suspension form, was given orally in three equal doses, for each animal for seven consecutive days.

Dose selection and administration: 5 ml of AHB-1 preparation/kg of animal body weight/day was selected to mimic the intended dose for humans. The intended dosage to be orally administered to babies is 5 ml of AHB-1 preparation/kg of body weight/day in three equal doses, for a maximum period of 5–7 days.

OBSERVATIONS

OBSERVATIONS INCLUDE

General activity.

Weight gain or loss.

Food and water intake.

Examination of excreta.

LABORATORY AND PATHOLOGY TESTS

At the end of the treatment period (7 days) 4 rabbits were sacrificed from both the treated and control given groups. At necropsy, sections of liver and kidney were selected for histological examination. Tissues were fixed in a 10 ml formaline solution and sent for pathological examination. The other animals (minus one rabbit from the treated group which fell from its cage accidentally and died), were kept for further observation period of 2 weeks then sacrificed and tissues were sent to pathology. Blood samples were collected from animals and a complete blood count and measurement of hemoglobin were conducted.

RESULTS OF EXAMPLES 3 AND 4

LD50 STUDY (TEST ON MICE)

Since a dose of 15 gm/kg of body weight of the mice did not result in any death in the treated group, then the LD50 of AHB-1 preparation is above 15 gm/kg and can be classified as relatively harmless. (Cassarett and Doull's Toxicology, "Basic Science of Poisons").

ACUTE STUDY (TEST ON RABBITS)

General observations: During the seven days of the experiment, none of the animals exhibited any sign of constipation or diarrhea, oliguria or polyuria. There was however a relative increase in the activity of the treated animals as compared to control animals (more movements).

No statistical differences were found in the amount of water or food intake or the urine output between treated and control animals, using t test at 0.05 level.

There were no pathological abnormalities or changes between tested animals and controls (Tables 1, 2).

Hematology: results include hemoglobin and complete blood cell count, all of which showed no statistically significant differences between treated and control animals. (Tables 3, 4).

CONCLUSION OF EXAMPLES 3 AND 4

DEALING WITH TESTS FOR THE TOXICITY OF AHB PREPARATION

The conclusion of all tests carried out in Examples 3 and 4 revealed that AHB-1 preparation is free from harmful effects on the tested animals. It is expected that all other AHB preparations can be classified as relatively harmless.

TABLE 1

ILLUSTRATIONS OF THE RESULTS OF PATHOLOGICAL TESTING OF THE TREATED RABBITS

| CASE NO. | LIVER | KIDNEY | TIME OF PATHOLOGICAL STUDY |
|---|---|---|---|
| R1 | N.D.A.R. | N.D.A.R. | 4 treated rabbits were sacrificed at the end of 7 days treatment. |
| R2 | N.D.A.R. | N.D.A.R. | |
| R3 | N.D.A.R. | N.D.A.R. | |
| R4 | N.D.A.R. | FOCAL MILD INTERSTITIAL INFLAMMATION | |
| R5 | DIED ACCIDENTALLY (FELL FROM ITS CAGE) | | |
| R6 | FOCAL MINIMAL PORTAL TRACT INFLAMMATION | FOCAL MILD INTERSTITIAL INFLAMMATION | 5 treated rabbits were sacrificed two weeks after stopping the treatment. |
| R7 | FOCAL MINIMAL PORTAL TRACT INFLAMMATION | N.D.A.R. | |
| R8 | GRANULOMATA. | N.D.A.R. | |
| R9 | GRANULOMATA. | N.D.A.R. | |
| R10 | N.D.A.R. | FOCAL AGGREGATES OF LYMPHOCYTES. | |

N.D.A.R.: No Diagnostic Abnormality Recognized.

TABLE 2

ILLUSTRATIONS OF THE RESULTS OF PATHOLOGICAL TESTING OF THE CONTROL GROUP RABBITS

| CASE NO. | LIVER | KIDNEY | TIME OF PATHOLOGICAL STUDY |
|---|---|---|---|
| C1 | FOCAL MINIMAL PORTAL TRACT INFLAMMATION. | FOCAL MILD INTERSTITIAL INFLAMMATION. | 4 control group rabbits were sacrificed at the end of 7 days observation. |
| C2 | N.D.A.R. | N.D.A.R. | |
| C3 | FOCAL MINIMAL PORTAL TRACT INFLAMMATION | FOCAL MILD INTERSTITIAL INFLAMMATION. | |
| C4 | FOCAL MINIMAL PORTAL TRACT INFLAMMATION | FOCAL MILD INTERSTITIAL INFLAMMATION. | |
| C5 | N.D.A.R. | N.D.A.R. | 6 control group rabbits were sacrificed after three weeks of observation. |
| C6 | FOCAL MINIMAL PORTAL TRACT INFLAMMATION. | FOCAL MILD INTERSTITIAL INFLAMMATION. | |
| C7 | MILD PORTAL TRACT INFLAMMATION | N.D.A.R. | |
| C8 | MODERATE PORTAL TRACT INFLAMMATION, MILD FATTY INFILTRATION. | FOCAL INTERSTITIAL HYALINIZATION + MILD INFLAMMATION. SOME TUBULES ARE CYCLICALLY DILATED. | |
| C9 | VERY MILD PORTAL TRACT INFLAMMATION, MILD FATTY INFILTRATION. | FOCAL MILD INTERSTITIAL INFLAMMATION. | |
| C10 | MILD PORTAL | FOCAL MILD | |

TABLE 2-continued

ILLUSTRATIONS OF THE RESULTS OF PATHOLOGICAL TESTING OF THE CONTROL GROUP RABBITS

| CASE NO. | LIVER | KIDNEY | TIME OF PATHO-LOGICAL STUDY |
|---|---|---|---|
| | TRACT INFLAMMATION. | INTERSTITIAL INFLAMMATION. | |

C: CONTROL
N.D.A.R.: NO DIAGNOSTIC ABNORMALITY RECOGNIIED.

TABLE 3

RESULTS OF BLOOD COUNT OF TREATED RABBITS

| NO. | WBC | RBC | HB | HCT | MCV | MCH | MCHC |
|---|---|---|---|---|---|---|---|
| R1 | 11.9 | 5.94 | 12.7 | 39.6 | 66.6 | 21.3 | 32.0 |
| R2 | 9.4 | 7.40 | 16.2 | 48.2 | 63.8 | 21.4 | 33.6 |
| R3 | 7.5 | 6.51 | 13.0 | 39.4 | 60.5 | 19.9 | 33.0 |
| R4 | 8.2 | 5.24 | 11.6 | 35.7 | 65.2 | 22.1 | 32.4 |
| R6 | 6.9 | 6.06 | 12.0 | 36.4 | 60.1 | 19.8 | 32.9 |
| R7 | 3.3 | 5.98 | 13.0 | 39.4 | 65.9 | 21.8 | 33.0 |
| R8 | 6.7 | 5.85 | 11.6 | 36.4 | 62.2 | 19.8 | 31.8 |
| R9 | 8.5 | 5.83 | 12.9 | 38.1 | 65.3 | 22.1 | 33.8 |
| R10 | 7.2 | 5.06 | 10.5 | 33.1 | 65.5 | 20.8 | 31.8 |
| AVERAGE | 7.7 | 5.98 | 12.6 | 38.5 | 63.9 | 21.0 | 32.7 |

TABLE 4

RESULTS OF BLOOD COUNT OF CONTROL RABBITS

| NO. | WBC | RBC | HB | HCT | MCV | MCH | MCHC |
|---|---|---|---|---|---|---|---|
| C1 | 5.8 | 5.72 | 13.5 | 38.1 | 66.4 | 23.6 | 35.5 |
| C2 | 5.2 | 5.53 | 12.8 | 35.5 | 64.1 | 23.3 | 36.3 |
| C3 | 10.5 | 5.59 | 12.9 | 37.6 | 67.3 | 23.0 | 34.2 |
| C4 | 11.1 | 5.28 | 12.5 | 35.3 | 66.8 | 23.6 | 35.3 |
| C5 | 6.2 | 6.71 | 14.1 | 40.5 | 60.4 | 21.0 | 34.7 |
| C6 | 10.5 | 6.83 | 13.6 | 40.5 | 59.3 | 19.9 | 33.6 |
| C7 | 8.7 | 7.53 | 10.8 | 46.7 | 62.0 | 22.3 | 36.0 |
| C8 | 7.6 | 6.23 | 14.8 | 43.4 | 69.7 | 23.8 | 34.2 |
| C9 | 8.2 | 5.45 | 12.7 | 34.8 | 63.8 | 23.3 | 36.6 |
| C10 | 4.5 | 5.75 | 12.1 | 35.0 | 60.9 | 21.0 | 34.5 |
| AVERAGE | 7.83 | 6.06 | 12.98 | 38.7 | 64.0 | 22.4 | 35.0 |
| NORMAL VALUES OF RABBITS | 7.9 | 6.29 | 13.0 | 39.8 | 64.0 | 21.0 | 33.0 |

N.B.:
WBC: White blood cells
RBC: Red blood cells
HB: Hemoglobin
HCT: Hematocrit
MCV: Mean corpuscular volume
MCH: Mean corpuscular hemoglobin
MCHC: Mean corpuscular hemoglobin concentration

EXAMPLE 5

CLINICAL STUDY

This study was done on 200 newborns including inpatients, outpatients and caesarean section newborns (Cs).

T.S.B. rises normally during the first few days of life up to 3–6.5 mg/dL. It drops once again to below 2 mg/dL after the first week of life.

T.S.B. was measured in all serums by capillary method using bilirubin analyzer (BIL.ANALYZER).

Phototherapy was administered in all study cases by Phototherapy unit with these specifications:

FL20BW-NU Lamp×4 ea
Total Energy: 10,440 cal/h
400–500 nm Energy: 5,600 cal/h

Inpatient and outpatient newborns with moderate to high T.S.B. have undergone a 'treatment study'. Whereas, caesarean section newborns have undergone a 'prophylactic study'. Caesarean newborns were selected to do prophylactic study because their stay at hospital is relatively long and can be observed closely.

I INPATIENTS (treatment study using AHB preparation and phototherapy)

AHB-1 preparation was administered in gel form at a dosage of 5 ml/kg of body weight/day in three equal doses.

The phototherapy was administered by phototherapy unit.

(a) Those with high T.S.B. (over 20% mg/dL)

11 newborns have undergone this study. The average drop in T.S.B. for 9 newborns during the 1st 24 hrs was 0.298 mg/dL/hr. Only in two cases with bilirubin 29 and 22 mg/dL exchange transfusions were carried out and AHB-1 preparation was given at the same time. No rebound increase in T.S.B. after exchange was noticed and there was no need for further exchanges.

(b) Possible Rh and ABO incompatibility 13 newborns have undergone this study. Modification, stabilization and decrease in T.S.B. (i.e. slow increase then decrease, no increase then decrease or immediate decrease in T.S.B.) took place. None of these newborns needed exchange transfusion.

(c) Prematures 8 newborns have undergone this study. Results are similar to (b) above.

(d) Newborns with NHB of miscellaneous causes 28 newborns have undergone this study. Results are also similar to (b) above.

II OUTPATIENTS (treatment study using only AHB-1 preparation)

80 newborns have undergone this study. AHB-1 preparation was administered in gel form at a dosage of 5 ml/kg of body weight/day in three equal doses.

In possible Rh and ABO incompatibility, in premature babies and in babies with NHB of miscellaneous causes as breast milk jaundice, starvation jaundice, cephalhematoma and jaundice of unknown etiology (36% of cases of NHB), there was modification, stabilization and decrease in T.S.B. The newborns did not need any further treatment apart from AHB-1 preparation.

III PROPHYLAXIS IN Cs. NEWBORNS

60 Cs. newborns have undergone this study. These were average newborns and each was given three doses 5 ml each of AHB-1 preparation in gel form, at the age of 6 hours, 14 hours and 22 hours.

Average T.S.B. after 3 days was 6.16 mg/dL, and most cases have T.S.B. below 10 mg/dL except for one baby whose T.S.B. was 10.4 mg/dL.

When AHB-1 preparation is given early to newborns, it causes rapid expulsion of meconium. Meconium weighs about 200 gms, in average newborn and contains 175 mg bilirubin 50% of which is indirect bilirubin (5–10 times the daily production of bilirubin by the newborn). In the fetus, the intestinal route for bilirubin elimination is not functioning. The fetus eliminates bilirubin via placenta and maternal circulation, and bilirubin is conjugated by maternal glucuronyl transferase enzyme. After birth maternal elimination of bilirubin stops. A major part of bilirubins in meconium is reabsorbed especially if there is delayed meconium excretion. Early administration of AHB-1 preparation after birth causes rapid treatment and expulsion of meconium and bilirubins, thus preventing re-absorption of meconium bilirubins and this causes prevention or modification of NHB. Additional value of early administration of AHB-1 preparation is the immediate energy given to the newborn after the stress of delivery. This energy is important for the vital centers of the brain, liver enzymes and gastrointestinal tract functions. The other preparations are expected to have the same effects.

In addition to the 60 Cs. newborns, an additional 15 average Cs. newborns who did not undergo any treatment were studied. Average T.S.B. after 3 days was 7.4 mg/dL and 3 of them had T.S.B. above 10 mg/dL.

EXAMPLE 6

MEAN DROP OF BILIRUBIN IN mg/dL/hr

INPATIENTS: (Table—5)

10 full term average newborns with neonatal jaundice and without hemolytic data were studied. Newborns received phototherapy and AHB-1 preparation in gel form which was administered at a dosage of 5 ml/kg of body weight/day in three equal doses. Hours under treatment and phototherapy were 576 hours. The mean drop in bilirubin in mg/hr. was 0.157 mg/dL/hr.

OUTPATIENTS: (Table—6)

10 full term average newborns with neonatal jaundice and without hemolytic data were studied. Newborns received only AHB-1 preparation in gel form which was administered at a dosage of 5 ml/kg of body weight/day in three equal doses. Total course of treatment with preparation was 432 hours. Mean drop in bilirubin in mg/hr. was 0.077 mg/dL/hr.

TABLE 5

CHARACTERISTICS OF BILIRUBIN CHANGE UNDER PHOTOTHERAPY AND AHB-1 PREPARATION

| CASE NO. | HOUR'S UNDER TREATMENT | BILIRUBIN AT THE BEGINNING OF STUDY mg/dL | BILIRUBIN AT THE END OF STUDY mg/dL | DECREASE OF BILIRUBIN PER hr. |
|---|---|---|---|---|
| 1 | 60 | 22.8 | 9.8 | 0.217 |
| 2 | 96 | 22.0 | 14.0 | 0.0083 |
| 3 | 48 | 22.5 | 14.0 | 0.177 |
| 4 | 72 | 12.0 | 11.0 | 0.014 |
| 5 | 60 | 22.5 | 12.0 | 0.175 |
| 6 | 48 | 22.0 | 10.0 | 0.250 |
| 7 | 48 | 18.0 | 12.0 | 0.125 |
| 8 | 48 | 17.0 | 13.0 | 0.083 |
| 9 | 36 | 19.0 | 9.0 | 0.278 |
| 10 | 60 | 18.2 | 8.2 | 0.167 |
| TOTAL | 576 | | | 1.569 |

AVERAGE DROP OF BILIRUBIN UNDER PHOTOTHERAPY AND AHB-1 PREPARATION IN mg/dL/hr = 0.157

TABLE 6

CHARACTERISTICS OF BILIRUBIN CHANGE UNDER AHB-1 PREPARATION ONLY

| CASE NO. | HOUR'S UNDER TREATMENT | BILIRUBIN AT THE BEGINNING OF STUDY mg/dL | BILIRUBIN AT THE END OF STUDY mg/dL | DECREASE OF BILIRUBIN PER hr. |
|---|---|---|---|---|
| 1 | 24 | 8.0 | 6.0 | 0.083 |
| 2 | 96 | 10.0 | 2.5 | 0.078 |
| 3 | 72 | 9.0 | 8.20 | 0.011 |
| 4 | 72 | 12.0 | 11.0 | 0.014 |
| 5 | 24 | 10.0 | 8.20 | 0.075 |
| 6 | 48 | 11.0 | 8.50 | 0.052 |
| 7 | 24 | 12.0 | 8.80 | 0.133 |
| 8 | 24 | 14.2 | 12.5 | 0.071 |
| 9 | 24 | 16.0 | 13.0 | 0.125 |
| 10 | 24 | 15.5 | 12.5 | 0.125 |
| TOTAL | 432 | | | 0.767 |

AVERAGE DROP OF BILIRUBIN UNDER AHB-1 PREPARATION ONLY IN mg/dL/hr = 0.077

EXAMPLE 7

COMPARISON STUDY

Pilot study was carried out on 20 newborns, having the same clinical conditions. These clinical conditions were the same age, the same weight and approximately the same T.S.B. level. Newborns were divided into two groups.

GROUP ONE 10 newborns, age 2–5 days, with T.S.B. range 12–16 mg/dL.

These were treated as outpatients and took only AHB-1 preparation in gel form which was administered at a dosage of 5 ml/kg of body weight/day in three equal doses.

Total hours of treatment were 396 hours.

Total drop in bilirubin was 33 mg.

Average drop of bilirubin was 0.088 mg/dL/hour.

GROUP TWO 10 newborns, age 2–5 days, with T.S.B. range 12.1–17 mg/dL. These were hospitalized and were treated only by phototherapy.

Total hours of exposure were 552 hours.

Total drop in bilirubin was 33.8 mg.

Average drop of bilirubin was 0.066 mg/dL/hour.

RESULTS

The average drop in T.S.B. in group one is 133% of that of group two.

EXAMPLE 8

IN VITRO STUDY

METHOD

Fifteen tests were carried out on 15 different samples of newborn serums with high bilirubin. In each test 200 microliter of serum were mixed with 200 microliter of AHB-1 preparation (in suspension form). Mixtures were then shaken for 30 seconds and kept away from light for: half an hour, one hour, three hours and six hours.

Centrifugation was done for 5 minutes for each mixture. The serum was separated and bilirubin was measured by the Bil-Analyzer.

RESULTS

The average drop in bilirubin after exposure was:

| | |
|---|---|
| After ½ hr exposure | 36% |
| After 1 hr. exposure | 53% |
| After 3 hr. exposure | 68% |
| After 6 hr. exposure | 73% |

The average drop in bilirubin from the 3rd to 6th hr. was only 5%.

EXAMPLE 9

Two newborns were treated with the preparation comprising castor oil, cellulose fibers, magnesium and vitamin $B_2$ in combination with phototherapy. The average drop of bilirubin for the two newborns in mg/dL/hr are 0.125 and 0.159.

EXAMPLE 10

CLINICAL STUDY

This study was done on 30 inpatient and outpatient newborns, who had high T.S.B. levels.

T.S.B. was measured in all serums by capillary method using bilirubin analyzer (BIL.ANALYZER).

Phototherapy was administered in all study cases by Phototherapy unit with these specifications:

FL20BW-NU Lamp×4 ea

Total Energy: 10,440 cal/h

400–500 nm Energy: 5,600 cal/h

I INPATIENTS (treatment study using AHB preparation and phototherapy)

The AHB preparation of Example 1C was administered in gel form at a dosage of 5 ml/kg of body weight/day in three equal doses.

The phototherapy was administered by phototherapy unit.

The drop in T.S.B. is 0.148 mg/dL/hr.

II OUTPATIENTS (treatment study using only AHB preparation)

The AHB preparation of Example 1C was administered in gel form at a dosage of 5 ml/kg of body weight/day in three equal doses.

The drop in T.S.B. is 0.073 mg/dL/hr.

We claim:

1. A method for treating or neonatal hyperbilirubinemia (NHB) by administering to an infant an antihyperbilirubinemia preparation consisting essentially of castor oil, cellulose fibers, magnesium and vitamin $B_2$ as active ingredients and physiologically acceptable additives, carriers or diluents.

2. The method of claim 1 wherein the preparation is administered to newborn infant.

3. The method of claim 1 wherein the active ingredients of the preparation comprise in weight percent:

Castor Oil: 10–50%,

Cellulose fibers: 3–9%, and 0.0010 to 0.0100 gm/100 gm preparation of magnesium and 0.00010 to 0.00100 gm/100 gm of preparation of vitamin $B_2$.

4. The method according to claim 1 wherein the amount of preparation administered daily is 5 ml/kg of body weight.

5. The method according to claim 4 wherein the amount of preparation is administered in three equal doses.

6. The method according to claim 1 wherein the preparation is administered for 5 to 7 days.

7. The method of claim 1 wherein the preparation is in gel form.

8. The method of claim 1 wherein the preparation is in suspension form.

9. The method of claim 1 wherein the preparation is administered orally.

10. The method of claim 1 wherein the preparation is administered with breast milk, humanized milk or infant formula.

11. A composition for treating or prophylactically treating neonatal hyperbilirubinemia consisting essentially of castor oil, honey and cellulose fibers as active ingredients said castor oil, honey and cellulose fibers being present in amounts of 10–50 weight % castor oil, 5–40 weight % honey, and 3–9 weight % cellulose fibers and physiologically acceptable additives, carriers or diluents.

12. A composition for treating or prophylactically treating neonatal hyperbilirubinemia consisting essentially of castor oil, cellulose fibers, magnesium and vitamin $B_2$ as active ingredients said castor oil, cellulose fibers, magnesium and vitamin $B_2$ being present in amounts of 10–50 weight % castor oil, 3–9 weight % cellulose fibers; 0.0010 to 0.100 gm/100 gm of the composition of magnesium and 0.00010 to 0.00100 gm/100 gm of the composition of vitamin $B_2$, and physiologically acceptable additives, carriers or diluents.

13. A method for preventing neonatal hyperbilirubinemia (NHB) by administering to infant at risk for developing neonatal hyperbilirubinemia an antihyperbilirubinemia preparation comprising castor oil, cellulose fibers, magnesium and vitamen $B_2$ as active ingredients and physiologically acceptable additives, carriers or diluents.

14. The method of claim 13 wherein the preparation is administered to newborn infant.

15. The method of claim 13 wherein the active ingredients of the preparation comprise in weight percent:

| | |
|---|---|
| Castor Oil | 10–50%, |
| Cellulose Fibers | 3–9% and |

0.0010 to 0.0100 gm/100 gm of preparation of magnesium and 0.00010 to 0.00100 mg/100 mg of preparation of vitamin $B_2$.

16. The method according to claim 13 wherein the amount of preparation administered daily is 5 ml/kg of body weight.

17. The method according to claim 16 wherein the amount of preparation is administered in three equal doses.

18. The method according to claim 16 wherein the preparation is administered for 5 to 7 days.

19. The method accordng to claim 13 wherein the preparation is in gel form.

20. The method according to claim 13 wherein the preparation is in suspension form.

21. The method according to claim 13 wherein the preparation is administered orally.

22. The method of claim 13 wherein the preparation is administered with breast milk, humanized milk or infant formula.

23. The method of claim 13 wherein magnesium is in the form of magnesium salts, magnesium oxide or physiologically acceptable forms of magnesium.

* * * * *